US005580717A

United States Patent [19]
Dower et al.

[11] Patent Number: 5,580,717
[45] Date of Patent: *Dec. 3, 1996

[54] RECOMBINANT LIBRARY SCREENING METHODS

[75] Inventors: William J. Dower, Menlo Park; Steven E. Cwirla, Palo Alto, both of Calif.

[73] Assignee: Affymax Technologies N.V., Curaco, Netherlands Antilles

[*] Notice: The term of this patent shall not extend beyond the expiration date of Pat. No. 5,427,908.

[21] Appl. No.: 376,326

[22] Filed: Jan. 20, 1995

Related U.S. Application Data

[63] Continuation of Ser. No. 517,659, May 1, 1990, Pat. No. 5,427,908.
[51] Int. Cl.[6] .............................. C12Q 1/68; C12Q 1/70; C07K 16/46; C12N 7/01
[52] U.S. Cl. .............................. 435/5; 435/235.1; 435/6; 435/69.7; 530/387.3; 530/395
[58] Field of Search .............................. 435/69.7, 235.1, 435/6, 5; 530/387.3, 395

[56] References Cited

U.S. PATENT DOCUMENTS

| | | | |
|---|---|---|---|
| 4,593,002 | 6/1986 | Dulbecco | 435/172.3 |
| 5,223,409 | 6/1993 | Ladner | 435/69.7 |
| 5,427,908 | 6/1995 | Dower et al. | 435/5 |

FOREIGN PATENT DOCUMENTS

| | | | |
|---|---|---|---|
| 469897 | 2/1992 | European Pat. Off. | |
| 2183661 | 6/1987 | United Kingdom | C12N 15/00 |
| 88/05085 | 7/1988 | WIPO | C12P 19/34 |
| 88/06630 | 9/1988 | WIPO | C12P 21/00 |
| 89/06694 | 7/1989 | WIPO | C12P 21/00 |
| 90/02809 | 3/1990 | WIPO | C12P 21/00 |
| 90/05144 | 5/1990 | WIPO | C07K 13/00 |
| 90/14424 | 11/1990 | WIPO | C12N 15/00 |
| 90/14430 | 11/1990 | WIPO | C12P 19/34 |
| 90/14443 | 11/1990 | WIPO | C12Q 1/70 |
| 91/10737 | 7/1991 | WIPO | C12N 15/13 |
| 91/18980 | 12/1991 | WIPO | C12N 15/00 |
| 92/01047 | 1/1992 | WIPO | C12N 15/00 |
| 92/07077 | 4/1992 | WIPO | C12N 15/34 |
| 92/06204 | 4/1992 | WIPO | C12N 15/64 |
| 92/15702 | 9/1992 | WIPO | C12Q 1/02 |
| 92/18619 | 10/1992 | WIPO | C12N 7/01 |

OTHER PUBLICATIONS

Aruffo and Seed (1987), Molecular Cloning of A CD28 cDNA By A High–Efficiency COS Cell Expression System, *Proc. Natl. Acad. Sci. USA* 84:8573–8577.
Barbas III et al. (1991), Assembly of Combinatorial Antibody Libraries On Phase Surfaces; The Gene III Site, *Proc. Natl. Acad. Sci. USA* 88:7978–7982.
Bass et al. (1990), Hormone Phage: An Enrichment Method For Variant Proteins With Altered Binding Properties, *Proteins: Structure, Function and Genetics* 8:309–314.
Better et al. (1988), *Escherichia Coli* Selection Of An Active Chimeric Antibody Fragment, *Science* 240:1041–1043.
Boeke and Model (1982), A Prokaryotic Membrane Anchor Sequence: Carboxyl Terminus of Bacteriophage f1 Gene III Protein Retains It In the Membrane, *Proc. Natl. Acad. Sci. USA* 79:5200–5204.
Cwirla et al. (1990), Peptides on Phage: A Vast Library of Peptides For Identifying Ligands, *Proc. Natl. Acad. Sci. USA* 87:6378–6382.
de la Cruz et al. (1988), Immumogenicity and Epitope Mapping Of Foreign Sequences Via Genetically Engineered Filamentous Phage, *J. Bol. Chem.* 263:4318–4322.
Devlin et al. (1990), Random Peptide Libraries: A Source Of Specific Protein Binding Molecules, *Science* 249:404–406.
Dower et al. (1988), High Efficiency Transformation Of *E. coli* By High Voltage Electroporation, *Nucl. Acids Res.* 16:6127–6145.
Dunn et al., "Improved peptide function from random mutagenesis over short 'windows,'" *Protein Engineering* 2:283–291 (1988) (see abstract; p. 284, left–hand column, lines 1–15).
Felici et al. (1991), Selection Of Antibody Ligands From a Large Library of Oligopeptides Expressed On A Multivalent Exposition Vector, *J. Mol. Biol.* 222:301–310.
Garrard et al. (1991), $F_{AB}$ Assembly and Enrichment In A Monovalent Phage Display System, *Bio/Tech.* 9:1373–1377.
Geysen et al. (1987), Strategies for Epitope Analysis Using Peptide Synthesis, *J. Immunol. Meth.* 102:259–274.
Goldsmith and Konigsberg (1977), Adsorption Protein Of The Bacteriophage fd: Isolation, Molecular Properties, And Location In The Virus, *Biochem.* 16:2686–2694.
Greenwood et al. (1991), Multiple Display Of Foreign Peptides On A Filamentous Bacteriophage, *J. Mol. Biol.* 220:821–827.
Hoogenboom et al. (1991), Multi–Subunit Proteins On The Surface Of Filamentous Phage: Methodologies For Displaying Antibody (Fab) Heavy And Light Chains, *Nucl. Acids Res.* 19:4133–4137.
Hoogenboom et al., "Building antibodies from their genes," *Immunol. Reviews* 130:41–68 (1992).
Huse et al. (1989), Generation Of A Large Combinatorial Library Of The Immunoglobulin Repertoire In Phage Lambda, *Science* 246:1275–1281.

(List continued on next page.)

*Primary Examiner*—Lila Feisee
*Attorney, Agent, or Firm*—Townsend & Townsend & Crew

[57] ABSTRACT

Nucleotide sequences encoding proteins of interest are isolated from DNA libraries using bacteriophage to link the protein to the sequence which encodes it. DNA libraries are prepared from cells encoding the protein of interest and inserted into or adjacent to a coat protein of a bacteriophage vector, or into a sequence encoding a protein which may be linked by means of a ligand to a phage coat protein. By employing affinity purification techniques the phage particles containing sequences encoding the desired protein may be selected and the desired nucleotide sequences obtained therefrom. Thus, for example, novel proteins such as monoclonal antibodies may be produced and conventional hybridoma technology avoided.

18 Claims, No Drawings

OTHER PUBLICATIONS

Huse Antibody Engineering. A Practical Guide (1992) (Carl A. K. Borrebaeck, ed., W. P. Freeman Co.).

Ilyichev et al. (1990), M13 Filamentous Bacteriophage In Protein Engineering, *Molekulyarnaya Biologiya* 24:530–535 (English translation).

Kang et al. (1991), Linkage Of Recognition And Replication Functions By Assembling Combinatorial Antibody Fab Libraries Along Phage Surfaces, *Proc. Natl. Acad. Sci. USA* 88:4363–4366.

Lemire et al. (1989), "The mitochondrial targeting function of randomly generated peptide sequences correlates with predicted helical amphiphilicity," *J. Biol. Chem.* 264:20206–20215.

McCafferty et al. (1990), Phage Antibodies: Filamentous Phage Displaying Antibody Variable Domains, *Nature* 348:552–554.

Oliphant et al. (1986), Cloning of Random-Sequence Oligodeoxynucleotides, *Gene* 44:177–183.

Parmley and Smith (1988), Antibody-Selectable Filamentous fd Phage Vectors: Affinity Purification Of Target Genes, *Gene* 73:305–318.

Parmley and Smith (1989), Filamentous Fusion Phage Cloning Vectors For The Study Of Epitopes And Design Of Vaccines, *Adv. Exp. Med. Biol.* 251:215–218.

Reidhaar-Olson et al., "Combinatorial cassette mutagenesis as a probe of the informational content of protein sequences," *Science* 24:53–57 (1988).

Scopsi et al., "Nonspecific immunocytochemical reactions with certain neurohormonal peptides and basic peptide sequences," *J. of Histochem. and Cytochem.* 34:1469–1475 (1986).

Scott et al. (1990), An Epitope Library, in *Advances in Gene Technology: The Molecular Biology of Immune Diseases and the Immune Response,* Proceedings of the 1990 Miami Bio/Technology Winter Symposia, eds. Streilein et al., IRL Press, New York, pp. 224.

Scott and Smith (1990), Searching For Peptide Ligands With An Epitope Library, *Science* 249:386–390.

Skerra and Pluckthun (1988), Assembly Of A Functional Immunoglobulin $F_v$ Fragment In *Escherichia coli, Science* 240:1038–1041.

Smith (1985), Filamentous Fusion Phage: Novel Expression Vectors That Display Cloned Antigens On the Virion Surface, *Science* 228:1315–1317.

Smith et al. (1990), An Epitope Library, in *J. of Cell. Biochem.,* Supp. 14C:246, Abs. CK319, UCLA Symposia on Molecular and Cellular Biology, 19th Annual Meetings, p. 246.

Soderlind et al., "Phage display technology in antibody engineering: design of phagemid vectors and in vitro maturation systems," *Immunol. Reviews* 130:109–124 (1992).

Ward et al. (1989), Binding Activities Of A Repertoire Of Single Immunoglobulin Variable Domains Secreted From *Escherichia coli, Nature* 341:544–546.

Winter et al., "Making antibodies by phage display technology," *Annu. Rev. Immunol.* 12:433–455 (1994).

Young and Davis (1983), Yeast Polymerase II Genes: Isolation With Antibody Probes, *Science* 222:778–782.

Zacher III et al. (1980), A New Filamentous Phage Cloning Vector: fd-tet, *Gene* 9:127–140.

RECOMBINANT LIBRARY SCREENING METHODS

This is a continuation of application Ser. No. 07/517,659 filed May 1, 1990, now U.S. Pat. No. 5,427,908.

FIELD OF THE INVENTION

The present invention relates generally to recombinant DNA technology and, more particularly, to methods for screening DNA libraries for DNA sequences that encode proteins of interest.

BACKGROUND OF THE INVENTION

Isolating a gene which encodes a desired protein from a recombinant DNA library can be a daunting task. Hybridization probes may facilitate the process, but their use is generally dependent on knowing at least a portion of the sequence of the gene which encodes the protein. When the sequence is not known, DNA libraries have been expressed in an expression vector and antibodies have been used to screen plaques or colonies for the desired protein antigen. This procedure has been useful in screening small libraries, but sequences which are represented in less than about 1 in $10^5$ clones are easily missed, and screening libraries larger than $10^6$ can be difficult.

Antibody molecules are comprised of light and heavy polypeptide chains, each having a distinct variable (V) region, the combination of which produces an antigen binding region. Based on random combination events of heavy and light chains in any one antibody-producing cell, the potential repertoire of antibody heavy and light chain combinations may be as much as $10^{12}$ or greater. Thus, to sample a large fraction of this repertoire and obtain clones which express an antibody having a desired antigen binding specificity, an extremely large library may have to be constructed and screened.

Methods are needed which facilitate the screening process, thereby enabling DNA sequences which encode proteins of interest, and particularly antibody molecules, to be more readily identified, recloned and expressed. Were such procedures available, it may become possible to probe an animal's entire antibody repertoire, for example, to obtained an antibody to a preselected target molecule. In this manner the difficulties and labor intensive process of generating monoclonal antibodies, regardless of the species of origin, by conventional hybridization or transformation of lymphoblastoid cells, may be avoided. Quite surprisingly, the present invention fulfills these and other related needs.

SUMMARY OF THE INVENTION

Methods are provided for screening a DNA library for a nucleotide sequence which encodes a protein of interest. The methods generally involve physically linking the protein of interest, in a biologically active form (usually having a binding activity), to the specific DNA sequence encoding that protein. This allows the isolation and identification of that DNA by means of affinity techniques relying on the binding activity of the protein of interest.

In one aspect of the invention a bacterial host cell is transformed or infected with a bacteriophage expression vector, which vector comprises a DNA library member joined to a first nucleotide sequence encoding a tag protein. The vector also contains a second nucleotide sequence that encodes a tag ligand peptide that specifically binds the tag protein, which second sequence is joined to a third nucleotide sequence encoding a coat protein of the bacteriophage particle. The transformed or infected host cell is then cultivated under conditions suitable for expression and assembly of the bacteriophage particles and the association of the tag protein with the tag ligand peptide on the surface of the phage particle. Particles which encode the protein of interest are then selected from the culture by an affinity enrichment technique. This is accomplished by means of a ligand specific for the protein of interest, such as an antigen if the protein of interest is an antibody. Repeating the affinity selection procedure provides an enrichment of clones encoding the desired sequences, which may then be isolated for sequencing, further cloning and/or expression.

In another embodiment the invention concerns methods for screening a DNA library expressing one or more polypeptide chains that are processed, folded and assembled in the periplasmic space to achieve biological activity. A non-lytic phage vector is preferred for this purpose. Particularly preferred examples of such vectors are the filamentous phage fd, f1 and M13. In this embodiment a library of DNA sequence members, each joined to a first nucleotide sequence coding for a tag protein, is cloned into an appropriate location of the phage genome, behind an appropriate promoter and translation sequences and a sequence encoding a signal peptide leader directing transport of the downstream fusion protein to the periplasmic space. The phage vector also contains a second DNA sequence inserted into a coat protein gene to express a tag ligand peptide acting as a ligand for the tag protein, which peptide is expressed in a location of the coat protein exposed to the external environment of the phage and, so, is accessible for binding by the tag protein. In a preferred embodiment this peptide is located at or near the N-terminus of the pIII coat protein. The protein(s) of interest are expressed and transported to the periplasmic space, and the properly assembled proteins are adsorbed to the phage particle by virtue of the interaction of the tag protein with the ligand peptides on the phage as the phage particles are extruded from the cell. Phage bearing the desired protein are then selected by means of a ligand specific for the protein of interest.

In yet another embodiment the invention concerns methods for screening a DNA library whose members are joined to a nucleotide sequence encoding a coat protein of a bacteriophage vector. The phage may be a filamentous phage, such as, for example, fd, f1, or M13. Typically the DNA library sequences are inserted in the 5' region of a gene which encodes a phage coat protein, such as pIII. Thus, a phage coat protein fused to a DNA library member-encoded protein is produced and assembled in to the viral particle. For those proteins whose activity requires more than one chain, the second and any subsequent chain(s) are expressed from the phage genome so as to be transported to the periplasm where they assemble with the first chain that is fused to the phage coat protein, which complex associates with the phage particle as it exits the cell. Phage particles which encode the protein of interest are selected by means of a ligand specific for the protein.

DESCRIPTION OF THE SPECIFIC EMBODIMENTS

Methods and compositions are provided by the present invention for conveniently identifying clones of desired recombinantly-produced proteins. A method of affinity enrichment allows for the screening of libraries to identify clones having desired ligand specificities, where up to about $10^9$ or more clones may be readily screened. This represents a significant improvement over the art, where conventional procedures typically allow about $10^6$ clones in a DNA library to be screened, sometimes up to $10^7$ clones but with proportionate increases in time and labor.

In one aspect the invention involves linking the desired protein, such as an antibody molecule, to the DNA which encodes it. By then enriching for the protein, such as by affinity techniques, for example, the DNA which encodes the protein is also enriched and may then be isolated. The DNA so obtained may then be cloned and expressed in other systems, yielding potentially large quantities of the desired protein, or may be subjected to sequencing and further cloning and genetic manipulations prior to expression.

The protein for which the DNA is enriched and cloned according to the present invention is typically an antibody or fragment thereof, but may also be any protein which may be cloned from a nucleotide library. In addition to antibodies, such proteins may include, for example, growth hormones, interferons, interleukins, hormones, enzymes, zymogens, etc. Proteins which may be cloned are those for which specific binding partners (e.g. antigen or hapten when the desired protein is an antibody) have been identified.

When the protein of interest is an antibody of a desired binding specificity, the antibody may be of any of the known isotypes or subclasses for a particular species, and may be a single-chain or two-chain binding complex or portion thereof. For instance, only the variable antigen-binding regions of heavy ($V_H$) and/or light ($V_L$) chains may be identified and cloned; the binding fragments ($F_v$) or Fab encoded thereby may find use either as a binding fragment, joined to constant regions of heavy or light chains, or joined to other proteins having desired effector functions. The characteristics of the constant region domains will depend to a large extent on the use intended for the antibody, e.g., diagnostic and/or therapeutic applications, catalytic antibodies, etc.

Typically the protein's binding partner, e.g., an antigen or hapten when the protein is an antibody, is known, and the methods herein provide a means for creating and/or identifying a protein (and the DNA which encodes the protein) which specifically binds the binding partner of interest. Thus when the protein is an antibody the present invention provides a novel means for producing antibodies, particularly monoclonal antibodies, to predetermined antigens and antigenic determinants, thereby circumventing the laborious, time-consuming and often unpredictable process of conventional monoclonal antibody technology. Although murine monoclonal antibody production is often relatively straightforward, it is labor intensive. Furthermore, the development of human monoclonal antibodies by conventional approaches has been hampered by a variety of technical difficulties which, to a large extent, would be circumvented by the present invention.

According to the present invention, a DNA library is prepared from cells which are capable of encoding the desired protein. A variety of techniques exist for preparing the library, which may be prepared from either genomic DNA or cDNA. See, e.g., Sambrook et al., *Molecular Cloning, A Laboratory Manual*, 2nd ed., Cold Spring Harbor Laboratory Press, Cold Spring Harbor, N.Y., 1989, which is incorporated herein by reference. It is understood that when referring herein to DNA it is meant to include both genomic and cDNA, unless otherwise specified. The cells which serve as the source of RNA or DNA may be any which are capable of encoding the protein of interest. Enrichment procedures and means for amplifying the regions containing the gene(s), if known, may be employed. For instance, when the desired protein is an antibody, RNA and cDNA may be prepared from spleen cells from unimmunized animals, from animals immunized with antigens or haptens of interest, hybridoma cells, or lymphoblastoid cells, for example. The use of spleen cells from unimmunized animals provides a better representation of the possible antibody repertoire, while spleen cells from immunized animals are enriched for sequences directed against epitopes of the immunizing antigen or haptens. The cells may be obtained from a variety of animal species, such as human, mouse, rat, lagomorpha, equine, bovine, avian, etc., the selection often dependent on the protein of interest and the use for which it is intended.

Amplification of sequences representing messenger RNA (mRNA) isolated from cells of interest, such as spleen or hybridoma cells, may be performed according to protocols outlined in, e.g., U.S. Pat. No. 4,683,202, Orlandi, et al. *Proc. Natl. Acad. Sci. USA* 86:3833–3837 (1989), Sastry et al., *Proc. Natl. Acad. Sci. USA* 86:5728–5732 (1989), and Huse et al. Science 246:1275–1281 (1989), each incorporated herein by reference. Oligonucleotide primers useful in amplification protocols may be unique or degenerate or incorporate inosine at degenerate positions. Thus, for multichain immunoglobulins, primers would be generally used for amplification of sequences encoding the variable regions of both the heavy and light chains. Restriction endonuclease recognition sequences may be incorporated into the primers to allow for the cloning of the amplified fragment into a vector in a predetermined reading frame for expression.

Expression libraries containing the amplified cDNA are typically prepared in a vector such as a bacteriophage. The characteristics of the suitable bacteriophage depends on the specific embodiment employed, and will generally be those which conveniently allow insertion of the recombinant DNA into host cells by in vitro packaging or genetic transformation, which infect host cells capable of expressing the desired proteins, and whose DNA contains restriction sites, useful for cloning, which are located in regions of the phage genome where insertion of foreign DNA will not substantially disrupt essential functions of the phage.

Thus, in one embodiment of the invention whereby the protein is processed and assembled into a functional form and associates with the bacteriophage particles within the cytoplasm of the host cell, bacteriophage λ and derivatives thereof are examples of suitable vectors. When used for expression of antibody sequences, such as $V_H$, $V_L$, $F_v$ (variable region fragment) or Fab, library DNA may be inserted into λ vector, as described generally by Huse et al., supra, and Short et al., *Nucleic Acids Res.* 16:7583 (1988). The vector may be designed to be asymmetric with respect to restriction sites that flank the cloning and expression sequences. This asymmetry allows efficient recombination of libraries coding for separate chains of the active protein.

When the desired protein is an immunoglobulin, a library expressing antibody light chain binding regions may be combined with one expressing antibody heavy chain binding regions, thereby constructing combinatorial antibody or Fab expression libraries. For instance, one λ vector is designed to serve as a cloning vector for antibody light chain sequences, and another λ vector is designed to serve as a cloning vector for antibody heavy chain sequences in the initial steps of library construction. A combinatorial library is constructed from the two λ libraries by crossing them at an appropriate restriction site. DNA is first purified from each library, and the right and left arms of each respective λ vector cleaved so as to leave the antibody chain sequences intact. The DNAs are then mixed and ligated, and only clones that result from proper assembly of reciprocal vectors reconstitute as viable phage.

The invention also contemplates alternative methods for achieving efficient recombination of libraries encoding the separate protein chains. These alternatives include the use of multiple, rare cloning sites (e.g., Not I and Sfi I) used in subcloning sequences from one library into the other; or using phage vectors which exist in double stranded, plasmid-like form at some point in their life cycle (e.g., replicative form "RF" DNA of filamentous phage), and to clone the separate libraries in different versions of the vector containing different cloning sites and different selectable markers (Amp® and Tet®, for example) The sequences from the separate libraries are joined so that a sequence of interest and a corresponding selectable marker from each library resides in each single phage genome. Application of double selection will enrich for those hosts harboring the combined phage genomes.

As mentioned, the vectors may be engineered to efficiently clone the library amplification products. For example, oligonucleotides may be used to introduce the asymmetric restriction sites, a ribosome binding site at an optimal distance for expression of the cloned sequence, and cloning sites for the library amplification products.

In certain embodiments of the invention at least one of the library-encoded protein chains is cloned into a vector so as to be expressed fused to a tag protein. As used herein, a "tag" protein is meant to refer to a protein which has a specific binding affinity for a peptide or protein ligand. For example, the tag protein should have specificity for a peptide or protein ligand of at least about 3 to about 100 or more amino acids, preferably with an affinity exceeding at least about $10^{-7}$ to $10^{-8}$M, and more preferably equal to or greater than about $10^{-9}$M. A tag protein with more than one binding site for the tag ligand peptide provides a resulting increase in avidity, which greatly decreases the dissociation rate and somewhat relaxes the requirement for affinity at each site (the affinity of each binding site may then be as low as about $10^{-6}$M). The tag protein should be preferably less than about 100 kD but may be more, and should be of a composition such that its fusion with the protein of interest, e.g., the N-terminus of the tag with the C-terminus of an antibody heavy chain fragment, does not interfere with the binding of tag protein to the tag ligand peptide. The tag protein should also be such that its presence on the C-terminus of the protein (e.g., antibody fragment) does not in general alter the specificity of, or seriously reduce the affinity of the protein for its ligand (e.g., of an antibody for its antigan).

A sequence encoding the tag peptide ligand is engineered into or adjacent to a gene encoding a bacteriophage coat protein so as to display the ligand on the outer surface of the phage particle. Thus, when the foreign library DNA is expressed as a fusion protein with the tag protein, the specific binding pair ligand member will be accessible to bind the tag/desired protein fusion protein. If the desired library encoded protein is a multi-chain protein, such as an antibody, generally only one of the chains preferably the heavy chain if an antibody) is expressed fused to the tag protein. To minimize interference with the antigan binding region of the antibody or fragment thereof (which binding is used in the panning procedure described further below to isolate the phage encoding the desired antibody or other protein of interest) the tag protein is typically fused at the heavy chain C-terminus or the C-terminus of the desired fragment.

The density of tagging of the phage particles may be controlled by expressing the ligand peptide in a plasmid carrying an additional copy of the phage protein expressed at the desired level. In this case only a portion of the proteins going into the assembly of the phage would contain the peptide ligand to the tag protein.

Host cells are then infected with the phage, and cultivated under conditions allowing for the expression and assembly of phage particles. The appropriate host cells for bacteriophage λ are various strains of *E. coli*, specific examples depending on which of the several suitable λ vectors is chosen. Of course, phage having bacterial hosts other than *E. coli* may also be used.

Under the appropriate induction, the library-encoded protein chain-tag (and other library-encoded chains if the protein is multi-chained) is expressed and allowed to assemble in the bacterial cytoplasm. It should be noted that the assembly of some multi-chain proteins, such as some antibodies, may be hindered to some extent in the bacterial cytoplasm. The induction of the protein(s) may be delayed until some replication of the phage genome, synthesis of some of the phage structural proteins, and assembly of some phage particles has occurred. The assembled protein chains then interact with the phage particles via the binding of the tag protein with its peptide ligand on the outer surface of the phage particle. The cells analysed and the phage bearing the library-encoded receptor protein (that corresponds to the specific library sequences carried in the DNA of that phage) are released and isolated from the bacterial debris. Once the cells lyse, any further binding of the antibodies to the phage should be prevented to minimize spurious binding between receptor protein and phage particles originating from different cells. Because the ligand peptide on the phage surface may be in excess, an amount of the tag protein is added to the cell suspension before lysis sufficient to bind and block unoccupied peptide on the surface of phage released from the cells.

To enrich for and isolate phage which contain cloned library sequences that encode a desired protein, and thus to ultimately isolate the nucleic acid sequences themselves, phage harvested from the bacterial debris are affinity purified. A ligand or binding partner specific for the desired cloned library protein is used in the affinity purification. For example, when the desired protein is an antibody which specifically binds a particular antigen or antigenic determinant, the antigen or determinant is used to retrieve phage having the desired protein on or a part of its outer surface. The ligand is typically adsorbed to an insoluble substrate, such as a particle or bead or plate. The phage so obtained may then be amplified by infecting into host cells. Additional rounds of affinity enrichment, as great as or greater than $10^4$ fold per round, and amplification may be employed until the desired level of enrichment is reached or the target phage are no longer enriched relative to the background phage.

The enriched antibody-phage are also screened with additional detection techniques such as expression plaque (or colony) lift (see, e.g., Young and Davis, *Science*, 222:778–782 (1983), incorporated herein by reference) whereby the same or another binding partner is used as a probe. Screening may employ additional assays (for a catalytic activity, for example) which are used to detect, in situ, plaques expressing proteins having the desired characteristics. The phage obtained from the screening protocol are infected into cells, propagated, and the phage DNA isolated and sequenced, and/or recloned into a vector intended for gene expression in prokaryotes or eukaryotes to obtain larger amounts of the particular protein selected.

In another embodiment, the library-encoded desired protein (or multiple chains comprising said protein) is transported to an extra-cytoplasmic compartment of the host cell, usually the periplasmic space, to facilitate processing and/or proper assembly. This may be preferred when the desired protein is an antibody or the antigen binding region of antibody heavy and light chains. When extra-cytoplasmic transport of the desired protein is employed, the sequences encoding one or more polypeptide chains of the protein are cloned adjacent to appropriate transcriptional and translational signals and signal peptide leaders that will direct the mature chains to the periplasm. As above, however, at least one of the chains is cloned adjacent to or within a tag protein so as to be expressed as a fusion of the protein of interest and the tag protein. In the case of antibody chain fragments, the tag is preferably fused to the C-terminus of the antibody chain (usually the heavy chain, but alternatively the light chain) to minimize interference with the antigen binding region. For other proteins the tag may be placed in an N-terminal or C-terminal location or internally, but in any event the tag protein should not substantially interfere with the ability of the protein of interest to bind a specific binding partner which is used in the affinity enrichment protocol described herein.

In the above embodiment a sequence that encodes a tag ligand peptide is engineered into a sequence encoding a phage coat protein. A suitable location for the ligand may be, for example, the N-terminal region of a coat protein, particularly that of a filamentous phage such as fd, f1, M13, etc. The coat protein is chosen for its ability to incorporate a tag ligand at or near the N- or C-terminal and yet be appropriately assembled into the coat of a phage particle.

A preferred example of this embodiment is the placement of a ligand peptide in the N-terminus region of the minor coat protein pIII of bacteriophage fd. Before incorporation into the phage, pIII resides in the inner membrane of the host cell with its N-terminus protruding into an extracytoplasmic compartment, probably the periplasm. In this configuration the tag ligand peptide in the N-terminus of pIII is available for binding to the tag protein fused to the protein of interest. This complex is then incorporated into the mature phage particle as it exits the cell and the C-terminus embeds in the coat of the phage.

Under conditions appropriate for expression of the library-encoded protein, tag protein and ligand-coat protein, the protein of interest is expressed and transported to the periplasmic space where conditions are conducive for proper processing, folding and assembly (as is the case for antibody chains). Because at least one chain of the assembled protein is fused to a tag protein, the assembled protein of interest binds to the phage particle via the tag ligand as phage are extruded from the cell. The phage bearing the active protein of interest are then isolated by the affinity enrichment method described below and the DNA coding for the protein of interest is thereby obtained.

In yet another embodiment, the desired protein is also transported to an extra-cytoplasmic compartment of the host cell, such as the bacterial periplasm, but as a fusion protein with a viral coat protein. In this embodiment the desired protein (or one of its polypeptide chains if it is a multi-chain protein, such as an antibody) is expressed fused to a viral coat protein which is processed and transported to the cell inner membrane. Other chains, if present, are expressed with a secretion leader and thus are also transported to the periplasm or other intracellular but extra-cytoplasmic location. The chains (e.g., light and heavy chains) present in the extra-cytoplasm then assemble into a complete protein (or binding fragment thereof). The assembled molecules become incorporated into the phage by virtue of their attachment to the phage coat protein as the phage extrude through the host membrane and the coat proteins assemble around the phage DNA. The phage bearing the antibody complex may then be screened by affinity enrichment.

In this embodiment the synthesis and amplification of cDNAs is prepared as described above, and then is cloned into or near a vector sequence encoding a coat protein, where the vector is, or is derived from, a filamentous phage, such as f1, fd, Pf1, M13, etc. In a preferred embodiment the filamentous phage is fd-tet. The phage vector is chosen to contain a cloning site located in the 5' region of a gone encoding a phage coat protein, such as, for example, the pIII coat protein. An appropriate vector (e.g., fd-tet B1 which is described below) allows oriented cloning of foreign sequences so that they are expressed at or near the N-terminus of the mature coat protein.

A library is constructed by cloning the cDNA (e.g., the $V_H$ region) from the donor cells into a coat protein gone (e.g., gene III, "gIII") cloning site. The cloned sequences of, for example, the $V_H$ domains are ultimately expressed as polypeptides or proteins (of up to about 120 amino acids in the case of the $V_H$ protein) fused to the N-terminus of the mature coat protein on the outer, accessible surface of the assembled phage particles. Although a large peptide fragment near the N-terminus of the coat protein may cause a decrease in the phage infectivity and/or yield compared to phage with much smaller, similarly-placed fragments, the larger fragments may still be effectively enriched by the procedures described herein.

Some peptides, because of their size and/or sequence, may cause severe defects in the infectivity of their carrier phage. This causes a loss of phage from the population during reinfection and amplification following each cycle of panning. To minimize problems associated with defective infectivity, DNA prepared from the eluted phage is transformed into host cells by electroporation or well known chemical means. The cells are cultivated for a period of time sufficient for marker expression, and selection is applied as typically done for DNA transformation. The colonies are amplified, and phage harvested as described below for a subsequent round(s) of panning.

When the desired protein is a multi-chain protein, such as an antibody or binding fragment thereof, the cDNA encoding the chain(s) not cloned into a phage coat protein may be cloned directly into an appropriate site (as described below) of the vector containing the first chain-coat protein library; or, preferably, the subsequent chain(s) may be cloned as a separate library in a different plasmid vector, amplified, and subsequently the fragments installed in the first chain-coat protein library vector. For example, when the first chain is an antibody heavy chain or binding fragment thereof, the ultimate destination of light chain $V_L$ cDNA sequence is in a vector phage RF DNA that already contains a $V_H$ sequence in a coat protein gene, thus randomly recombining $V_H$ and $V_L$ sequences in a single phage genome.

The second or subsequent chain of the desired multi-chain protein, such as $V_L$, is cloned so that it is expressed with a signal peptide leader sequence that will direct its secretion into the periplasm of the host cell. For example, several leader sequences have been shown to direct the secretion of antibody sequences in *E. coli*, such as OmpA (Hsiung, et al., *Biotechnology* 4:991–995 (1986)), pelB (Better, et al., *Science* 240:1041–1043 (1988)), phoA (Skerra and Pluckthun, *Science* 240:1038–1043 (1988)), and β-lactamase (Zemel-Dreasen and Zamir, *Gene* 27:315–322 (1984)).

The cloning site for the subsequent chain cDNA's should be placed so that it does not substantially interfere with normal phage function. One such locus is the intergenic region as described by Zinder and Boeke, *Gene* 19:1–10 (1982). The $V_L$ sequence is preferably expressed at an equal or higher level than the $V_H$/pIII product to maintain a sufficiently high $V_L$ concentration in the periplasm to provide efficient assembly (association) of $V_L$ with $V_H$ chains.

Generally, the successful cloning strategy utilizing a phage coat protein, such as pIII of filamentous phage fd, will provide: (1) expression of a protein chain (or a first polypeptide chain when the desired protein is multichained, e.g., the $V_H$ chain) fused to the N-terminus of a full sized (or nearly full sized) coat protein (e.g., pIII) and transport to the inner membrane of the host where the hydrophobic domain in the C-terminal region of the coat protein anchors the fusion protein in the membrane, with the N-terminus containing the chain protruding into the periplasmic space and available for interaction with a second or subsequent chain (e.g., $V_L$ to form an $F_v$ or Fab fragment) which is thus attached to the coat protein; (2) adequate expression of a second or subsequent polypeptide chain if present (e.g., $V_L$) and transport of this chain to the soluble compartment of the periplasm; and (3) will usually, but not necessarily, produce little or no interference with normal phage function or host cell viability.

The number of possible combinations of heavy and light chains probably exceeds $10^{12}$. To sample as many combinations as possible depends, in part, on the ability to recover large numbers of transformants. For phage with plasmid-like forms (as filamentous phage), electrotransformation provides an efficiency comparable to that of phage λ transfection with in vitro packaging, in addition to a very high capacity for DNA input. This allows large amounts of vector DNA to be used to obtain very large numbers of transformants. The method described by Dower et al., *Nucleic Acids Res.*, 16:6127–6145 (1988), incorporated by reference herein, may be used to transform fd-tet derived recombinants at the rate of about $10^7$ transformants/µg of ligated vector into *E. coli* (such as strain MC1061), and libraries may be constructed in fd-tet B1 of up to about $3\times10^8$ members or more. Increasing DNA input and making modifications to the cloning protocol within the ability of the skilled artisan may produce increases of greater than about 10-fold in the recovery of transformants, providing libraries of up to $10^{10}$ or more recombinants.

The transformants are selected by growth in an appropriate antibiotic(s) which, in the case of the fd-tet vector, is tetracycline. This may be done on solid or in liquid growth medium. For growth on solid medium, the cells are grown at a high density (~$10^8$ to $10^9$ tfs per m²) on a large surface of, for example, L-agar containing the selective antibiotic to form essentially a confluent lawn. The cells and extruded phage are scraped from the surface and phage are prepared for first round of panning essentially as described by Parmley and Smith, *Gene* 73:305–318 (1988), incorporated by reference herein. For growth in liquid culture, cells may be grown in L-broth and antibiotic through about 10 or more doublings. The phage are harvested by standard procedures (see Sambrook et al., (1989) *Molecular Cloning*, 2nd ed. (1989), supra, for preparation of M13 phage) as further modified as described below. Growth in liquid culture may be more convenient because of the size of the libraries, while growth on solid media likely provides less chance of bias during the amplification process.

For affinity enrichment of desired clones, about $10^3$ to $10^4$ library equivalents (a library equivalent is one of each recombinant—$10^4$ equivalents of a library of $10^9$ members is $10^9 \times 10^4 = 10^{13}$ phage) are incubated with hapten (ligand) to which the desired protein (e.g., antibody) is sought. The hapten is in one of several forms appropriate for affinity enrichment schemes. In one example the hapten is immobilized on a surface or particle, usually anchored by a tether of enough length (3 to 12 carbons, for example) to hold the hapten far enough away from the surface to permit free interaction with the antibody combining site. The library of phage bearing antibodies is then panned on the immobilized hapten generally according to the procedure described in the Example section below.

A second example of hapten presentation is hapten attached to a recognizable ligand (again with a tether of some length). A specific example of such a ligand is biotin. The hapten, so modified, is incubated with the library of phage and binding occurs with both reactants in solution. The resulting complexes are then bound to streptavidin (or avidin) through the biotin moiety. The streptavidin may be immobilized on a surface such as a plastic plate or on particles, in which case the complexes (phage-antibody-hapten-biotin-streptavidin) are physically retained; or the streptavidin may be labelled, with a fluorophore, for example, to tag the active phage/antibody for detection and/or isolation by sorting procedures, e.g., on a fluorescence-activated cell sorter.

The phage bearing antibodies without the desired specificity are removed by washing. The degree and stringency of washing required will be determined for each protein of interest. A certain degree of control can be exerted over the binding characteristics of the antibodies recovered by adjusting the conditions of the binding incubation and the subsequent washing. The temperature, pH, ionic strength, divalent cations concentration, and the volume and duration of the washing will select for antibodies within particular ranges of affinity for the hapten. Selection based on slow dissociation rate, which is usually predictive of high affinity, is the most practical route. This may be done either by continued incubation in the presence of a saturating amount of free hapten, or by increasing the volume, number, and length of the washes. In each case, the rebinding of dissociated antibody-phage is prevented, and with increasing time, antibody-phage of higher and higher affinity are recovered.

Additional modifications of the binding and washing procedures may be applied to find antibodies with special characteristics. The affinities of some antibodies are dependent on ionic strength or cation concentration. This is a useful characteristic for antibodies to be used in affinity purification of various proteins when gentle conditions for removing the protein from the antibody are required. Specific examples are antibodies which depend on $Ca^{++}$ for binding activity and which released their haptens in the presence of EGTA. See Hopp et al., *Biotechnology* 6:1204–1210 (1988). Such antibodies may be identified in the recombinant antibody library by a double screening technique isolating first those that bind hapten in the presence of $Ca^{++}$, and by subsequently identifying those in this group that fail to bind in the presence of EGTA.

Antibodies with certain catalytic activities may be enriched in groups of antibodies with high affinity for reactants (substrates and intermediates) but low affinity for products. A double screen to enrich for antibodies with these characteristics may be useful in finding antibodies to catalyze certain reactions. Further, catalytic antibodies capable of certain cleavage reactions may also be selected. One category of such reactions is the cleavage of a specific end group from a molecule. For example, a catalytic antibody to cleave a specific amino acid from an end of a peptide may be selected by immobilizing the peptide and panning the antibody library under conditions expected to promote binding but not cleavage (e.g., low temperature, particular ionic strength, pH, cation concentration, etc., depending on the nature of the end group and the cleavage reaction) and followed by a wash. This allows antibodies that recognize the end group to bind and become immobilized, and from this group will come those capable of cleavage. To find those capable of cleavage, the conditions are shifted to those favorable for cleavage. This step will release those antibody-phage capable of cleaving themselves free of the immobilized peptide.

An alternative way to accomplish this is to pan for antibodies that bind to the specific end group by attaching that end group to a bond different from that to be cleaved (a non-peptide bond, for example). By subsequent panning (of the positive phage from the first screen) on the end group attached via the proper bond under cleavage conditions, the non-binding fraction will be enriched for those with the desired catalytic activity.

To elute the active antibody-phage from the immobilized hapten, after washing at the appropriate stringency, the bound (active) phage are generally recovered by eluting with pH shift. For example, pH2 or pH11 may be used, which is then neutralized and the eluted phage are amplified by infecting or transforming the host cells. Examples of such hosts are E. coli, MC1061-F'KAN or K91. The cells are then grown as tetracycline resistant colonies. The colonies are scraped up and the extruded phage are purified by standard procedures as before. These phage are then used in another round of affinity enrichment (panning), and this cycle is repeated until the desired level of enrichment is reached or until the target phage are no longer enriched relative to the background phage. Repeated rounds of panning and intervening amplifications can provide levels of enrichment exceeding $10^7$-fold. To isolate individual clones, phage from the final round of panning and elution are infected into cells or their DNA is transformed into cells and grown on agar (usually L-agar) and antibiotics (usually tet) to form well separated individual colonies, each of which is a clone carrying phage genomes with both $V_H$ and $V_L$ sequences. The single stranded DNA from phage particles extruded from each colony may be isolated and DNA coding for the $V_H$ and $V_L$ fragments sequenced. The replicative form of the phage DNA (double stranded) may be isolated by standard means and the DNA in the cloning sites ($V_H$ and $V_L$ sequences) recloned into a vector designed for gene product expression in prokaryotes or eukaryotes to obtain larger amounts of the particular antibodies selected in the screening process.

Phage identified as having an antibody recognized by the target ligand are propagated as appropriate for the particular phage vector used. For fd-tet this is done in a liquid culture of rich medium (L-broth, for example) with antibiotic (Tet) selection. The phage are harvested and DNA prepared and sequenced by standard methods to determine the DNA and amino acid sequence of the particular antibody.

The DNA may be recloned in a suitable eukaryotic or prokaryotic expression vector and transfected into an appropriate host for production of large amounts of protein. Antibody is purified from the expression system using standard procedures. The binding affinity of the antibody is confirmed by well known immunoassays with the target antigen or catalytic activity as described in Harlow and Lane, *Antibodies, A Laboratory Manual,* Cold Spring Harbor, N.Y. (1988), incorporated herein by reference.

The following example is offered by way of illustration, not by way of limitation.

EXAMPLE I

This Example describes a procedure for isolating an antibody which binds to a preselected antigen, and thereby isolating the nucleotide sequences which encode the antibody. An immunoglobulin expression library is prepared from mouse spleen cells using a filamentous phage, fd. The antibody heavy chains are expressed as fusion proteins with coat protein pIII. Phage particles which contain the antibody of the desired binding specificity are isolated by means of a panning procedure using the preselected antigen.

Construction of Vectors

A filamentous bacteriophage vector, fdTetB1, was constructed from the tetracycline resistance transducing vector fdTet (Zacher et al., 1980). The cloning site in fdTetB1 was engineered into the N-terminal region of gene III, and comprises two noncomplementary BstXI sites separated by 18 bases. This was accomplished by first removing a BstXI restriction site that was already present in the TN10 region of fdTet. RF DNA was digested with BstXI restriction endonuclease, followed by the addition of T4 polymerase to remove the protruding 3' termini. Blunt ended molecules were then ligated and electrotransformed into MC1061. RF DNA was isolated from several tetracycline resistant transformants and was digested with BstXI restriction endonuclease. A clone which was not digested with this enzyme was selected for insertion of the cloning site by site directed mutagenesis (Kunkel et al., *Meth. Enzymol.,* 154:367–382 (1987)) with the oligonucleotide 5'TATGAGGTTTTGCCA-GACAACTGGAACAGTTTCAGCGGA GTGCCAGTA-GAATGGAACAACTAAAGG-3'. Insertion of the correct mutagenic sequence was confirmed by dideoxy sequencing of RF DNA that was isolated from several tetracycline resistant transformants.

Construction of Degenerate Oligonucleotide Library

Vector fdTetBSN was constructed to contain a pair of non-complementary SfiI sites in the TN10 region. This site is the ultimate destination of the expression cassette from the light chain library. fdTetB1 was opened at the unique HindIII site. Two synthetic, complementary oligonucleotides were kinased and annealed to form the structure

```
AGCTGGCCGCAGCGGCCGCGGCCGCGGCCGGTCCGGCC
    CCGGCGTCGCCGGCGCCGGCGCCGGCCAGGCCGGTCGA
```

This oligo was ligated to the HindIII site of fdTetB1 by standard methods. A properly ligated and circularized molecule should contain no HindIII sites, so after inactivating the ligase, the reaction was recut with HindIII to linearize those plasmids that had not taken up an insert. This material was then transformed into *E. coli* and selected on tetracycline. The structure of the resulting molecules was verified and these were designated fdTetBSN.

To construct the vector fdTetSXNS, fdTetBSN was opened at the BstXI sites and an oligonucleotide, annealed to give the following structure

```
GCC TCG AGA GCA CGA CGT ACT AGT GCT TGT
A GAT CGG AGC TCT CGT GCT GCA TGA TCA CG
``` was ligated to the BstXI sites of fdBSN to provide unique XhoI and SpeI sites to receive the heavy chain fragments.

The plasmid vector pVL was constructed by digesting pUC19 with AlwNI and polishing the ends to bluntness. An SfiI site was introduced by ligating the annealed oligonucleotides

```
GGCCGCAGCGGCC
CCGGCGTCGCCGG
``` to the blunted AlwNI site.

The AatII site of this modified pUC19 was opened and a fragment containing the light chain expression cassette described by Huse et al., flanked on the downstream side (with respect to transcription) by an SfiI site of the sequence GGCCGGTCCGGCC. This plasmid now contains (in clockwise direction) SfiI site, B-lactamase gene, a lac Z promoter, a ribosome binding site, a pel B signal peptide sequence, SacI site, XbaI site, translation termination site(s), and SfiI site.

Construction of the separate heavy and light chain libraries cDNA sequences representing the antigen binding domains of the heavy and light antibody chains are synthesized from the RNA of antibody producing cells in the manner described by Huse et al., supra. Spleen cells are used from mice that have been immunized with the preselected antigen to which the desired antibody binds. The cDNA is amplified by PCR using primers annealing to the regions common to many antibody sequences that flank the variable antigen binding domains. The primers also contain appropriate restriction site sequences as described below. The amplified, double-stranded fragments are digested with the appropriate restriction nucleases and ligated to the compatible sites in the respective vectors. For the heavy chain fragments this is accomplished by the incorporation of XhoI sites into the 5'-PCR primers and SpeI sites into the 3'-primers. These sites are then exposed by digestion and ligated to the corresponding sites in the digested fdTetSXNS vector. The ligation products were transformed by electroporation into E. coli MC1061 and, after outgrowth, selected on tetracycline.

For the light chain library, the light chain fragments are amplified with 5'-PCR primers containing SacI sites and 3'-primers containing XbaI sites. The sites on the fragments are opened and ligated to the corresponding sites in pVL. The ligation products are then transformed by electroporation into E. coli MC1061. After outgrowth, transformants were recovered by selection on ampicillin.

Construction of the combined heavy-light chain expression library

DNA from the light chain library (in pVL) was digested with SfiI. The larger of the two resulting fragments, which contains the light chain expression cassette, is isolated and ligated in several-fold molar excess to DNA of the heavy chain library (in fdTetSXNS) that has been digested with SfiI. The ligation products are transformed by electroporation into E. coli MC1061 cells. After a period of outgrowth, the transformants are double-selected on ampicillin (100 ug/ml) and tetracycline (20 ug/ml). The resulting transformants constitute combined library of heavy and light chain fragments in fdTetSXNS.

The methods of cDNA synthesis, restriction digestions, fragment phosphorylation, and ligation are essentially as prescribed in Sambrook et al., supra. In all cases, DNA to be transformed is ethanol precipitated in the presence of 0.3M sodium acetate and resuspended in water. Electrotransformations are done as described by Dower et al., supra. After 1 hour of non-selective outgrowth at 37° C. in SOC medium (2% Bacto tryptone, 0.5% Bacto yeast extract, 10 mM NaCl, 2.5 mM KCl, 10 mM MgCl2, 10 mM MgSO4, 20 mM glucose) and an aliquot is removed and several dilutions are plated on LB plates containing the appropriate antibiotic (20 ug/ml tetracycline, 100 ug/ml ampicillin, or both). The remainder of the transformation is used to inoculate one liter of L-broth containing the appropriate antibiotic and is grown for various times to amplify the library. Phage are isolated from this culture and stored at 4° C.

Isolation of Phage

Purified phage from liquid cultures are obtained by clearing the supernatant two times by centrifugation, and precipitating phage particles with polyethylene glycol (final concentration 3.3% polyethylene glycol 8000, 0.4M NaCl). Following centrifugation, phage pellets are resuspended in TBS (50 mM Tris-HCl, pH 7.5, 150 mM NaCl) and stored at 4° C. Phage are also isolated from plate stocks in this manner, after scraping colonies from the agar surface and resuspending in L-broth.

Affinity Purification

Approximately $10^3$–$10^4$ library equivalents of phage are reacted overnight with 1 µg purified antibody at 4° C. The mixture is panned by a procedure as follows. A 60×15 mm polystyrene petri plate is coated with 1 ml of streptavidin solution (1 mg/ml in 0.1M NaHCO$_3$, pH 8.6, 0.02% NaN$_3$) and is incubated overnight at 4° C. The following day the streptavidin solution is removed. The plate is filled with 10 ml blocking solution (30 mg/ml BSA, 3 µg/ml streptavidin in 0.1M NaHCO$_3$, pH 9.2, 0.02% NaN$_3$) and incubated for 2 hours at room temperature. Two micrograms of biotinylated goat anti-mouse IgG (BRL) are added to the antibody-reacted phage library and incubated for 2 hours at 4° C. Immediately before panning, blocking solution is removed from streptavidin coated plate, and the plate is washed 3 times with TBS/0.05% Tween 20. The antibody-reacted phage library is then added to the plate and incubated for 30 minutes at room temperature. Streptavidin coated agarose beads (BRL) may also be used for this affinity purification. The phage solution is removed and the plate is washed ten times with TBS/0.05% Tween 20 over a period of 60 minutes. Bound phage are removed by adding elution buffer (1 mg/ml BSA, 0.1N HCl, pH adjusted to 2.2 with glycine) to the petri plate and incubating for 10 minutes to dissociate the immune complexes. The eluate is removed, neutralized with 2M Tris (pH unadjusted) and used to infect log phase F'-containing bacterial cells. These cells are then plated on LB agar plates containing tetracycline (20 µg/ml), and grown overnight at 37° C. Phage are isolated from these plates as described and the affinity purification process was repeated for two to three rounds. After the final round of purification, a portion of the eluate is used to infect cells and plated at low density on LB tetracycline plates. Individual colonies are transferred to culture tubes containing 2 ml LB tetracycline and grown to saturation. Phage DNA is isolated using a method designed for the Beckman Biomek Workstation (Mardis and Roe., *Biotechniques,* 7:840–850 (1989)) which employs 96-well microtiter plates. Single stranded DNA is sequenced by the dideoxy method using Sequenase (U.S. Biochemicals) and an oligonucleotide sequencing primer (5'-CGATCTAAAGTTTTGTCGTCT-3') which is complementary to the sequence located 40 nucleotides 3' of the second BstXI site in fdTetB1.

It is evident from the above that compositions and methods are provided which substantially increase the ability to isolate nucleotide sequences which encode proteins of interest, particularly antibodies, from a large DNA library. This is especially encouraging, in that these methods and compositions may be employed to recover or produce de novo many proteins, and particularly monoclonal antibodies, useful as therapeutic or prophylactic compositions, diagnostic reagents, catalytic compounds, etc. previously obtainable only by extensive experimentation, if at all. The invention herein provides a means to circumvent many of the difficulties associated with traditional methods of monoclonal antibody technology, and particularly human monoclonal antibody technology. Further, the proteins identified by the present invention are produced by recombinant means, providing additional advantages of, inter alia, convenience, substantial purity and economics.

Although the foregoing invention has been described in some detail by way of illustration and example for purposes of clarity of understanding, it will be obvious that certain changes and modifications may be practiced within the scope of the appended claims.

What is claimed is:

1. A method for screening a DNA library for nucleotide sequences which encode a FAB fragment comprising first and second polypeptide chains, one of which chains comprises a heavy chain variable region and the other of which chains comprises a light chain variable region, which FAB fragment binds specifically to a ligand of interest, said method comprising:

(a) effecting filamentous bacteriophage expression vector transformation of a host cell with:

(i) a first nucleotide sequence that encodes a fusion coat protein comprising of the first polypeptide chain fused to a coat protein of the bacteriophage; and (ii) a second nucleotide sequence that encodes the second polypeptide chain fused to a signal peptide that directs periplasmic secretion of said second polypeptide chain;

(b) cultivating the transformed host cell under conditions suitable for expression and assembly of a bacteriophage particle with a coat comprising said fusion coat protein bound to said second polypeptide chain to form said FAB fragment on the coat of said bacteriophage particle; and (c) selecting said bacteriophage particle encoding the FAB fragment that binds specifically to the ligand of interest by binding said bacteriophage particle to the ligand specific for said FAB fragment and removing particles that do not bind to said ligand.

2. The method of claim 1, wherein the coat protein is encoded by gIII of the filamentous phage.

3. The method of claim 1, wherein the filamentous phage is selected from the group consisting of f1, fd, and M13 filamentous bacteriophage expression vectors.

4. The method of claim 3, wherein said filamentous bacteriophage expression vector is fd.

5. The method of claim 1, wherein the fusion coat protein comprises an antibody heavy chain variable region.

6. The method of claim 1, wherein the fusion coat protein comprises an antibody light chain variable region.

7. The method of claim 1, wherein the bacteriophage are isolated from the host cell after the expression and assembly of bacteriophage particles and before the selecting step.

8. The method according to claim 1, wherein expression of the antibody Fab fragment is inducible.

9. The method of claim 8, wherein the transformed host cell is lysed after cultivation and bacteriophage particles are isolated from cellular debris and then selected by binding said particles to a ligand specific for said antibody Fab fragment and removing particles that do not bind to said ligand.

10. The method of claim 9, wherein the bacteriophage particles which contain the nucleotide sequences encoding the antibody Fab fragment are enriched by repeating the selection step at least once.

11. The method of claim 10 further comprising the step of isolating the nucleotide sequences which encode the antibody Fab fragment from the selected bacteriophage particle.

12. The method of claim 1, wherein from $10^7$ to $10^9$ host cells are transformed by electroporation with $10^7$ to $10^9$ filamentous bacteriophage expression vectors wherein said vectors differ from one another with respect to the antibody Fab fragment encoded by each vector.

13. The method of claim 1, wherein the fusion coat protein comprises an antibody heavy chain variable region.

14. The method of claim 1, wherein the fusion coat protein comprises an antibody light chain variable region.

15. The method of claim 13, wherein said antibody heavy chain variable region is located at the amino terminus of said fusion coat protein on said bacteriophage surface.

16. The method of claim 14, wherein said antibody light chain variable region is locked at the amino terminus of said fusion coat protein.

17. The method of claim 1, wherein the first chain is fused to the N-terminus of the coat protein.

18. A filamentous phage displaying a FAB fragment comprising first and second polypeptide chains, one or which comprises a heavy chain variable region and the other a light chain variable region, which FAB fragment binds specifically to a ligand of interest; wherein the first chain is fused to a coat protein on the outersurface of the phage and the second chain is complexed with the first chain.

\* \* \* \* \*